United States Patent [19]

Biedermann et al.

[11] Patent Number: 5,833,998
[45] Date of Patent: *Nov. 10, 1998

[54] TOPICAL COMPOSITIONS FOR REGULATING THE OILY/SHINY APPEARANCE OF SKIN

[75] Inventors: Kimberly Ann Biedermann, Cincinnati; Donald Lynn Bissett, Hamilton; George Endel Deckner, Cincinnati, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 554,067

[22] Filed: Nov. 6, 1995

[51] Int. Cl.$^6$ ..................................................... A61K 7/48
[52] U.S. Cl. ..................... 424/401; 424/701; 514/844; 514/846; 514/944
[58] Field of Search .................................. 424/401, 701; 514/844–846, 944

[56] References Cited

U.S. PATENT DOCUMENTS

| | | | |
|---|---|---|---|
| 3,188,275 | 6/1965 | Erlemann | 167/87.1 |
| 4,087,550 | 5/1978 | Bouillon et al. | 424/319 |
| 4,210,654 | 7/1980 | Bauer | 424/263 |
| 4,329,338 | 5/1982 | Szego et al. | 424/180 |
| 4,505,896 | 3/1985 | Bernstein | 424/164 |
| 4,607,101 | 8/1986 | Bernstein | 514/24 |
| 4,840,790 | 6/1989 | Grollier et al. | 424/70 |
| 4,938,960 | 7/1990 | Ismail | 424/195.1 |
| 4,970,220 | 11/1990 | Chaussee | 514/358 |
| 5,234,926 | 8/1993 | Chandraratna | 514/253 |
| 5,415,861 | 5/1995 | Duffy et al. | 424/401 |
| 5,571,503 | 11/1996 | Mausner | 424/59 |

FOREIGN PATENT DOCUMENTS

| | | |
|---|---|---|
| 001079 | 3/1979 | European Pat. Off. . |
| 095615 | 12/1983 | European Pat. Off. . |
| 250300 | 12/1987 | European Pat. Off. . |
| 0489581A2 | 6/1992 | European Pat. Off. . |
| 0589047A1 | 3/1994 | European Pat. Off. . |
| 0628308A1 | 12/1994 | European Pat. Off. . |
| 1341454 | 12/1963 | France . |
| 1352978 | 1/1964 | France . |
| 3203M | 3/1965 | France . |
| 1588770 | 3/1970 | France . |
| 2210380 | 7/1974 | France . |
| 1467925 | 1/1969 | Germany . |
| 2242553 | 7/1974 | Germany . |
| 38 01 034 | 7/1989 | Germany . |
| 20 32006 | 2/1990 | Japan . |
| 1042499 | 9/1966 | United Kingdom . |
| 2210789 | 6/1989 | United Kingdom . |
| 2230186 | 10/1990 | United Kingdom . |
| 91/14431 | 10/1991 | WIPO . |
| WO 92/19217 | 11/1992 | WIPO . |
| 93/08017 | 4/1993 | WIPO . |
| 93/25213 | 12/1993 | WIPO . |

OTHER PUBLICATIONS

Abstract; Chemical Abstracts vol. 108, 1988, RO 92,889 (Nov. 30, 1987).
Beauty Counter, vol. 0, No. 0, ISSN: 0960–3751, p. 36, Nov. 1993.
International Product Alert, vol. 0, No. 0, p. N/A, Apr. 1, 1992.
International Product Alert, vol. 0, No. O, p. N/A, Nov. 3, 1993.
Marketing Brief: Nivea Visage Product Additions, The Rose Sheet, vol. 14, No. 29, Jul. 19, 1993.
Commercial Product Information—Max Factor Hyd. Oil Balancing Formulation; product content analysis, 1982.
J6 3022–510A, Jul. 14, 1986, Japan A61K, 07, Derwent Abstract No. 88–067978/10 only.
JP 63–60910, Mar. 17, 1988, Japan, A61K, 7/0, Abstract WPI Acc. No. 88–115373/17, English language Application identifying Info and Claims only.
Velikii et al., *Ukr. Biokhim Zh 50:368–371,* (1978) (untranslated); English language abstract therefor.
Wheatley et al., "Sebaceous Gland Differentiate: III. The Uses and Limitations of Freshly Isolated Mouse Preputial Gland Cells for the in vitro Study of Hormone and Drug Action", *J. of Invest. Derm.,* 76:293–296, 1981.
Cunliffe et al., "The Effect of Inhibitors of Cholesterol Synthesis of Sebum Secretion in Patients With Acne", *Br. J. Derm.,* 81(#4):280–282, 1969.
Rader et al., "Hepatic Toxicity of Unmodified and Time–Release Preparations of Niacin", *The Amer. J. of Med.,* 92:77–81, 1992.
Shalita et al., "Topical Nicotinamide Compared with Clindamycin Gel in the Treatment of Inflammatory Acne Vulgaris", *Int'l J. of Derm.,* 34(6):434–437, 1995.
Newstrom, "Nutrients Catalog", *McFarland & Co., Inc.,* pp. 11,23–24, 36–37, 43–44. 49–50, 58, 67–69, 89, 1993.
Shalita et al., "The Effects of Topical Nicotinamide on Acne Vulgaris", *JID,* 98:604, Abstracts 318, 1992.
Sheldon, *The Doctors' Vitamin and Mineral Encyclopedia,* Simon & Schuster, NY, pp. 49–82 (1991).
Manufacturer's Product Info. sheet: Asebiol LS2539B, Serobiologiques S. A. Laboratories (published before Nov. 6, 1995).

(List continued on next page.)

Primary Examiner—Jyothsna Venkat
Attorney, Agent, or Firm—Loretta J. Henderson; George W. Allen; David L. Suter

[57] ABSTRACT

Disclosed are topical compositions for regulating the oily and/or shiny appearance of skin. The compositions contain:
(a) an active for regulating the oily and/or shiny appearance of skin, said active consisting essentially of one or more compounds selected from the group consisting of niacinamide, pyridoxine, panthenol, and pantothenic acid, in an amount that is safe and effective for regulating the oily and/or shiny appearance of the skin; and
(b) a cosmetically acceptable carrier for said active. Also disclosed are methods of regulating the oily and/or shiny appearance of skin by topical application of such compositions.

10 Claims, No Drawings

OTHER PUBLICATIONS

Product Composition label Info.: Nivea Visage Hydro–Cleansing Gel (published before Nov. 6, 1995.

Product Composition label Info.: Nivea Visage Alcohol–Free Moisturizing Facial Toner (published before Nov. 6, 1995).

Product Composition label Info.: Nivea Visage Gentle Cleansing Lotion (published before Nov. 6, 1995).

Product Composition label Info.: Adrien Arpel Oil Control Moisturizer SPF15 (published before Nov. 6, 1995).

Product Composition label Info.: Clarins Creme de Soins Hydratante Teintee Moisturizing Tint SPF 6 (published before Nov. 6, 1995).

Product Composition label Info.: Clarins Fluide Multi–Confort Super Hydratant, Hydration–Plus Moisture Lotion SPF15 (published before Nov. 6, 1995).

Product Composition label Info.: Clarins Fluide Multi–Confort Super Hydratant, Hydration–Plus Moisture Lotion (published before Nov. 6, 1995).

Product Composition label Info.: Icone Peaux Seborrheiques Sebum Control Treatment (published before Nov. 6, 1995).

Product Composition Info.: Aveda Botanical Kinetics Pure Vital Moisture Eye Creme (published before Nov. 6, 1995).

Product Info.: Data Sheet, Papulex Gel, *Euroderma Limited* (published before Nov. 6, 1995).

Product Info.: Roche Product Data and Material Safety Data Sheet, Niacinamide, USP–FCC (published before Nov. 6, 1995).

TOPICAL COMPOSITIONS FOR REGULATING THE OILY/SHINY APPEARANCE OF SKIN

TECHNICAL FIELD

The present invention relates to topical compositions, and especially topical compositions for facial and scalp application. The topical compositions are particularly useful for regulating the oily and/or shiny appearance of skin.

BACKGROUND OF THE INVENTION

In the field of skin care compositions, the population is often classified by skin type, e.g., dry, normal, oily, combined dry/normal, combined dry/oily, or combined normal/oily skin (the latter two classes hereinafter alternatively referred to as "combined skin").

Persons with an oily skin type or combined skin type typically manifest an oily and/or shiny skin appearance between cleansings. This oily or shiny appearance generally increases as the day progresses following cleansing of the skin. In order to avoid such appearance, individuals must throughout the day either cleanse the skin, blot the skin, apply oil absorbing powders to the skin, or take some other measure to minimize the appearance of oil or shine.

Therefore, it has been desired in the art to provide topical compositions which minimize the appearance of oil and/or shine on the skin, especially oily or combined skin. Several topical compositions which are said to be designed for controlling oily and/or shiny skin are known in the art. For example, facial moisturizers and make-up said to have such property are known.

An oily or combined skin type presents a particular challenge to the formulation of make-up intended for facial use, including foundations. This is because as oil accumulates on the facial skin of such individuals, oil breakthrough occurs (the oil is not masked by the make-up such that an oily or shiny skin appearance results), and the coverage and wear resistance of the make-up tends to be reduced. It would be desirable to provide a make-up that maintains a high degree of coverage and wear resistance after application to all skin types, including oily and combined skin, preferably substantially as originally applied.

While certain formulations have been designed in an attempt to control the oily and/or shiny appearance of skin, there remains a need to provide improved topical compositions for minimizing the appearance of skin oil and/or shine. In addition to minimizing oil and/or shine, such compositions should not unacceptably discolor the skin. There is a particular need to provide improved facial make-up which minimizes the appearance of skin oil and/or shine, provides and maintains an even (i.e., uniform coverage) complexion and acceptable skin tone for extended periods after application, and/or which has extended wear resistance after application.

The B vitamins or vitamin B complex have heretofore been used to treat a number of conditions. For example, the following compounds have had the respective applications: riboflavin (acne, diabetes, anti-oxidant therapy, anemia, skin disorders, stress); nicotinic acid (atherosclerosis, pellegra, high cholesterol, high blood pressure, skin inflammation, antioxidant therapy); nicotinamide (pellegra, skin inflammation, anti-oxidant therapy); pantothenic acid (acne, anemia, arthritis, high cholesterol, atherosclerosis, alcohol detoxification, infections, hair loss); pyridoxine (acne, anemia, high cholesterol, skin inflammation, immune disorders, antioxidant therapy, carpal tunnel syndrome, premenstrual syndrome). These utilities and those of other B vitamin (complex) compounds are further described, along with a discussion of their contraindications and deficiency symptoms, in *The Doctor's Vitamin and Mineral Encyclopedia*, Hendler, S. S., pp. 49–82 (Simon & Schuster, New York 1990) and *Nutrients Catalog*, Newstrom, H., pp. 11–90 (McFarland & Co. 1993).

It has now been found that certain B vitamins are useful when topically applied for regulating the appearance of oily and/or shiny skin, including oily and combined skin, without unacceptably discoloring the skin, e.g., by unacceptable skin flushing or reddening. It has surprisingly been found that topical compositions containing these compounds in the form of a facial make-up composition minimize the appearance of skin oil and/or shine, provide and maintain substantially uniform coverage and an acceptable skin tone for extended periods after application, and/or have extended wear resistance after application.

It is an object of the present invention to provide topical compositions for regulating the oily and/or shiny appearance of mammalian skin, especially facial skin. It is a further object of this invention to provide such topical compositions which regulate the appearance of oily and/or shiny mammalian skin, provide and maintain substantially uniform coverage for extended periods after application to the skin, provide and maintain an acceptable skin tone for extended periods after application to the skin, and/or have extended wear resistance after application to the skin. Another object of the present invention is to provide methods of regulating the appearance of oily and/or shiny mammalian skin.

Other objects of the subject invention will be apparent from the disclosure which follows.

SUMMARY OF THE INVENTION

The present invention relates to topical compositions for regulating the oily and/or shiny appearance of mammalian skin, and especially facial skin. The compositions comprise a suitable active in an amount that is safe and effective for regulating the oily and/or shiny appearance of the skin, and a cosmetically acceptable topical carrier for the active. Preferred actives are those which effectively regulate the oily and/or shiny appearance of skin, and which do not unacceptably discolor the skin, e.g., unacceptably cause reddening or flushing of the skin. Suitable actives include those selected from the group consisting of niacinamide, pyridoxine, panthenol, pantothenic acid and mixtures thereof (these actives are alternatively referred to herein, individually or collectively, as "primary actives"). It has surprisingly been found that such actives, when topically applied to the skin, are especially useful for regulating the appearance of oily and/or shiny skin, including oily and combined skin, without unacceptably discoloring the skin, e.g., by unacceptable skin flushing or reddening. It has surprisingly been found that topical compositions containing these compounds in the form of a facial make-up composition minimize the appearance of skin oil and/or shine, provide and maintain substantially uniform coverage and acceptable skin tone for extended periods after application, and/or have extended wear resistance after application.

In preferred embodiments, the primary active comprises niacinamide. More preferably, the primary active consists essentially of niacinamide. Where niacinamide is used, it is preferably substantially pure niacinamide. The primary active is preferably used in an amount of from about 2.5% to about 5% by weight of the composition.

The present invention also relates to methods of regulating the oily and/or shiny appearance of mammalian skin by topical application of such compositions.

DETAILED DESCRIPTION OF PREFERRED EMBODIMENT

The compositions of the present invention are useful as topical compositions, i.e., they are suitable for topical administration to a biological subject such as a mammal. As used herein, "topical" means applied to the surface of the skin. The compositions of the subject invention are administered topically to a biological subject, i.e., by the direct laying on or spreading of the composition on the skin of the subject.

The topical compositions comprise a safe and effective amount of one or more primary actives and a cosmetically acceptable topical carrier for the primary actives.

As used herein "comprising" means that other steps and ingredients which do not affect the end result can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

As used herein, "safe and effective amount" means a sufficient amount of a compound, composition or other material described by this phrase to significantly induce a positive modification in the condition being treated, but low enough to avoid significant side effects (e.g., significant skin irritation or sensitization), within the scope of sound judgment of the skilled artisan. The safe and effective amount of the compound, composition or other material may vary with the particular skin being treated, the age and physical condition of the biological subject being treated, the severity of the condition, the duration of the treatment, the nature of concurrent therapy, the specific compound, composition or other material employed, the particular cosmetically acceptable topical carrier utilized, and like factors within the knowledge and expertise of the skilled artisan.

As used herein, "cosmetically acceptable" means that a material (e.g., compound or composition) which the phrase describes is suitable for use in contact with the tissues of humans and lower animals without undue toxicity, incompatibility, instability, irritation, allergic response and the like.

As used herein, "regulating the oily and/or shiny appearance of skin" means preventing, retarding and/or arresting the appearance of oil and/or shine on the skin. By regulating the oily and/or shiny appearance of the skin, one or more of the following benefits are achieved: there is a noticeable decrease in the visible oil, shine, or highlights on the skin, the skin is substantially free from visible oiliness, shine, or highlights; the skin has a substantially matte finish; the user has a more uniform complexion. Regulating the oily and/or shiny appearance of the skin may result in more uniform and lasting coverage of the skin by the composition, increased wear resistance of the composition and/or a decrease in the incidence or severity of skin oil breaking through the composition so as to become visibly apparent.

Unless otherwise stated, all percentages herein are weight percentages based on the weight of the composition.

As used herein, "mixtures" is meant to include a simple combination of materials and any compounds that may result from their combination.

Primary Actives

The compositions of this invention comprise one or more suitable primary actives in an amount that is safe and effective for regulating the oily and/or shiny appearance of the skin. Suitable actives are those which effectively regulate the oily and/or shiny appearance of skin without unacceptably discoloring the skin, e.g., unacceptably causing reddening or flushing of the skin.

Compounds that possess significant vasodilatory properties are typically unsuitable for use as a primary active. Such vasodilatory compounds tend to cause unacceptable flushing or reddening of the skin such that their use, especially in facial applications, is not desirable. For example, known vasodilators such as nicotinic acid are not suitable for use herein.

Preferred compositions of this invention comprise as primary actives one or more compounds selected from the group consisting of niacinamide, pyridoxine, panthenol, pantothenic acid, and mixtures thereof. In a preferred embodiment, the primary actives are substantially pure. By substantially pure it is meant that the compound described by that phase is at least 90% pure, at least more preferably 95% pure, most preferably 99% pure.

In a preferred embodiment, the primary active comprises niacinamide, which is more preferably substantially pure niacinamide. Thus, the primary active may consist essentially of:

(a) niacinamide; or (b) a mixture of (i) niacinamide and (ii) a compound selected from the group consisting of panthenol, pantothenic acid, and pyridoxine.

Preferably, the composition comprises from about 0.01% to about 20%, by weight, of primary active, more preferably from about 0.1% to about 10%, by weight, of primary active, even more preferably from about 1% to about 5%, by weight, of primary active, most preferably from about 2.5% to about 5%, by weight, of primary active, also from about 3% to about 5% primary active.

In an especially preferred embodiment, the topical composition comprises from about 2.5% to about 5%, by weight, of niacinamide, which is preferably substantially pure niacinamide.

Cosmetically Acceptable Carrier

The phrase "cosmetically acceptable carrier", as used herein, means one or more compatible solid or liquid fillers, diluents, extenders and the like, which are cosmetically acceptable as defined herein. The term "compatible", as used herein, means that the components of the compositions of this invention are capable of being comingled with the primary actives of the present invention, and with each other, in a manner such that there is no interaction which would substantially reduce the efficacy of the composition under ordinary use situations.

The type of carrier utilized in the present invention depends on the type of product desired. The topical compositions useful in the subject invention may be made into a wide variety of product types. These include, but are not limited to, lotions, creams, gels, sticks, sprays, ointments, pastes, mousses and cosmetics (e.g., solid, semi-solid, or liquid make-up, including foundations). These product types may comprise several types of carriers including, but not limited to, solutions, aerosols, emulsions (including oil-in-water or water-in-oil), gels, solids, and liposomes.

Solutions according to the subject invention typically include a cosmetically acceptable aqueous or organic solvent which is capable of having the primary active dispersed or dissolved therein. Water is a preferred solvent. Examples of suitable organic solvents include: propylene glycol, polyethylene glycol (e.g., Molecular Weight 200–600 g/mole), polypropylene glycol (e.g., Molecular Weight 425–2025 g/mole), glycerol, 1,2,4-butanetriol, sorbitol esters, 1,2,6-hexanetriol, ethanol, isopropanol, sorbitol esters, butanediol, and mixtures thereof. Solutions useful in the subject invention preferably contain from about 80% to about 99.99% of the aqueous or organic solvent and primary active in the above described amounts.

Aerosols according to the subject invention can be formed by adding a propellant to a solution such as described above. Exemplary propellants include chloro-fluorinated lower molecular weight hydrocarbons. Additional propellants that are useful herein are described in Sagarin, *Cosmetics Science and Technology,* 2nd Edition, Vol. 2, pp. 443–465 (1972), incorporated herein by reference. Aerosols are typically applied to the skin as a spray-on product.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers,* North American Edition, pages 317–324 (1986), each incorporated herein by reference.

The emulsion may also contain an anti-foaming agent to minimize foaming upon application to the skin. Anti-foaming agents include high molecular weight silicones and other materials well known in the art for such use.

Preferred emulsions have a low viscosity, of about 50 centistokes or less, more preferably about 10 centistokes or less, most preferably about 5 centistokes or less.

The topical compositions of the subject invention may comprise a topical cosmetically acceptable emollient. Such compositions preferably contain from about 2% to about 50% of the emollient. As used herein, "emollient" refers to a material used for the prevention or relief of dryness, as well as for the protection of the skin. A wide variety of suitable emollients are known and may be used herein. Sagarin, *Cosmetics, Science and Technology,* 2nd Edition, Vol. 1, pp. 32–43 (1972), incorporated herein by reference, contains numerous examples of materials suitable as an emollient.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and primary active in the above described amounts. A cream typically comprises from about 5% to about 50%, preferably from about 10% to about 20%, of emollient; from about 45% to about 85%, preferably from about 50% to about 75%, water; and primary active in the above described amounts.

In addition to the primary active, ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology,* 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and primary active in the above described amount.

Compositions of this invention useful for cleansing ("cleansers") are formulated with a suitable carrier, e.g., as described above, and preferably contain, in addition to the primary active in the above described amounts, from about 1% to about 90%, more preferably from about 5% to about 10%, of a cosmetically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers,* North American Edition (1986), published by Allured Publishing Corporation, which is incorporated herein by reference in its entirety. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a cosmetically acceptable carrier for the primary active and may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter, incorporated herein by reference.

The compositions of the present invention are preferably formulated to have a pH of 8 or below. The pH values of these compositions preferably range from about 2 to about 8, more preferably from about 3 to about 6, most preferably from about 4.5 to about 5.5.

Optional Ingredients

The compositions of this invention may contain other ingredients conventionally used in the art of skin care compositions, including but not limited to preservatives, preservative enhancers, and actives in addition to the primary actives. Any optional ingredients should be compatible with the primary active such that the activity of the primary active does not decrease unacceptably, preferably not to any significant extent, over a useful period (preferably at least about two years under normal storage conditions). For example, strong oxidizing agents may be incompatible with the primary active such that such agents are preferably avoided.

Other Actives

The compositions of the subject invention may optionally comprise other actives capable of functioning in different ways to enhance the benefits of the primary actives and/or to provide other benefits. Examples of such substances include, but are not limited to, anti-inflammatory agents, antimicrobial agents, anti-androgens, sunscreens, sunblocks, antioxidants/radical scavengers, chelators, depilation agents, desquamation agents, organic hydroxy acids, and natural extracts.

A. Anti-Inflammatory Agents

A safe and effective amount of an anti-inflammatory agent may be added to the compositions of the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), each incorporated herein by reference.

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the cosmetically acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

B. Retinoids

A safe and effective amount of a retinoid may be added to the compositions of the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid. The retinoid is preferably retinol, retinal, or retinoic acid, more preferably retinoic acid.

The retinoids enhance the skin appearance benefits of the present invention. For example, the retinoids may diminish fine lines, wrinkles, or other textural discontinuities. Such benefits are themselves desirable and in the present invention, tend to also improve application of the present compositions.

C. Antimicrobial Agents

As used herein, "antimicrobial agent" means a compound capable of destroying microbes, preventing the development of microbes or preventing the pathogenic action of microbes. Antimicrobial agents are useful, for example, in controlling acne. A safe and effective amount of an antimicrobial agent may be added to compositions of the subject invention, preferably from about 0.001% to about 10%, more preferably from about 0.01% to about 5%, also from about 0.05% to about 2% or from about 0.05% to about 1% of the compositions. Preferred antimicrobial agents useful in the subject invention are benzoyl peroxide, erythromycin, tetracycline, clindamycin, azelaic acid, and sulfur resorcinol.

D. Antiandrogens

As used herein, "anti-androgen" means a compound capable of correcting androgen-related disorders by interfering with the action of androgens at their target organs. The target organ for the subject invention is mammalian skin.

E. Sunscreens and Sunblocks

Exposure to ultraviolet light can result in excessive scaling and texture changes of the stratum corneum. Therefore, the compositions of the subject invention preferably contain a sunscreen or sunblock. Suitable sunscreens or sunblocks may be organic or inorganic.

A wide variety of conventional sunscreening agents are suitable for use herein. Sagarin, et al., at Chapter VIII, pages 189 et seq., of Cosmetics Science and Technology (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylacetoumbelliferone); trihydroxy-cimmamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; [3-(4'-methylbenzylidene bornan-2-one) and 4-isopropyl-di-benzoylmethane.

Of these, 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl)) aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy4-(2-hydroxyethoxy) benzophenone; 4-N,N-(2-ethylhexyl)-methylaminobenzoic acid ester of 4-(2-hydroxyethoxy) dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

Suitable inorganic sunscreens or sunblocks include metal oxides, e.g., zinc oxide and titanium dioxide. For example, the use of a titanium dioxide in topical sunscreen compositions that is applicable to the present invention is described in copending application Ser. No. 08/448,942, filed on May 24, 1995, in the names of Jiang Yue, Lisa R. Dew and Donald L. Bissett, incorporated herein by reference.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

F. Anti-Oxidants/Radical Scavengers

Preferred compositions of the subject invention include an anti-oxidant/radical scavenger as an active in addition to the primary active agents. The anti-oxidant/radical scavenger provides protection against UV radiation which can cause increased scaling or texture changes in the stratum corneum and against other environmental agents which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione) and dihydroxy fumaric acid and its salts may be used. Preferred anti-oxidants/radical scavengers are selected from tocopherol sorbate and other esters of tocopherol. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee, incorporated herein by reference.

G. Chelators

As used herein, "chelating agent" means an active agent capable of removing a metal ion from a system by forming a complex so that the metal ion cannot readily participate in or catalyze chemical reactions. The inclusion of a chelating agent provides protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. patent application Ser. No. 619,805, Bissett, Bush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the subject invention are furildioxime and derivatives thereof.

H. Organic Hydroxy Acids

The compositions of the present invention preferably comprise from 0.1% to about 10%, more preferably from about 0.2% to about 5%, also preferably from about 0.5% to about 2%, of an organic hydroxy acid such as salicylic acid, glycolic acid, or lactic acid. Salicylic acid is preferred. The organic hydroxy acids enhance the skin appearance benefits of the present invention. For example, the organic hydroxy acids tend to improve the texture of the skin.

J. Desquamation Agents

A safe and effective amount of a desquamation agent may be added to the compositions of the subject invention, preferably from about 0.1% to about 10%, more preferably from about 0.2% to about 5%, also preferably from about 0.5% to about 4% of the composition. Desquamation agents enhance the skin appearance benefits of the present invention. For example, the desquamation agents tend to improve the texture of the skin (e.g., smoothness). A variety of desquamation agents are known in the art and are suitable for use herein, including but not limited to the organic hydroxy agents described above. One desquamation system that is suitable for use herein comprises certain sulfhydryl compounds and certain zwitterionic surfactants and is described in copending application Ser. No. 08/480,632, filed on Jun. 7, 1995 in the name of Donald L. Bissett, incorporated herein by reference. Another desquamation system that is suitable for use herein comprises salicylic acid and certain zwitterionic surfactants and is described in copending patent application Ser. No. 08/209,401, filed on Mar. 9, 1994 in the name of Bissett.

K. Depilation Agents

The compositions of the present invention may include a safe and effective amount of a depilation agent. When used, the composition preferably contains from about 0.1% to about 10%, more preferably from about 0.2% to about 5%, also preferably from about 0.5% to about 2% of depilation agent. A depilation agent preferred for use herein comprises certain sulfhydryl compounds, e.g., N-acetyl-L-cysteine. The use of such depilation agents is described in more detail in copending application Ser. No. 08/479,878, filed on Jun. 7, 1995, in the name of Greg G. Hillebrand and Vladimir Gartstein, incorporated herein by reference.

L. Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art. Skin lightening agents suitable for use herein also include those described in copending patent application Ser. No. 08/479,935, filed on Jun. 7, 1995 in the name of Hillebrand; and copending patent application Ser. No.08/390,152, filed on Feb. 24, 1995 in the names of Kalla L. Kvalnes, Mitchell A. DeLong, Barton J. Bradbury, Curtis B. Motley, and John D. Carter; both incorporated herein by reference.

M. Other Combination Actives

The compositions of the present invention may also include a natural extract of yeast, rice bran or the like such as are known in the art. Such extracts enhance the skin appearance benefits of the present invention, and are preferably used in an amount of from 0.1% to about 20%, more preferably 0.5% to about 10%, also from 1% to about 5%. A natural extract of yeast is preferred.

In a preferred embodiment, the compositions of this invention comprise niacinamide, panthenol or a mixture thereof as primary active and a natural extract, preferably a natural extract of yeast.

The compositions preferably comprise an oil absorbent such as are known in the art, e.g. clays (e.g. bentonite), microsponges, and Polytrap.

Preparation of Compositions

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like.

Methods For Regulating the Oily/Shiny Appearance of Skin

The subject invention relates to methods of regulating the oily and/or shiny appearance of skin. Such methods comprise topically applying to the skin to be treated an effective amount of the compositions of the subject invention so as to deposit an effective amount of primary active on the skin. The term "effective amount", as used herein, means an amount sufficient to regulate the oily and/or shiny appearance of skin as defined herein. In general, a safe and effective amount of the primary actives are left in contact with the skin for a period sufficient to provide noticeable effects, generally after chronic application such as described herein.

The composition can be applied for several days, weeks, months or years at appropriate intervals. The compositions are preferably applied from about four times a day to about once every three days, more preferably from about twice a day to once every other day, also about once a day, until a satisfactory oily and/or shiny skin appearance improvement has been achieved. The regulation of the appearance of oily and/or shiny skin can be observed visually without magnification. Methods of quantifying the regulation of the appearance of oily and/or shiny skin such as are known in the art can also be employed, e.g., sebutape analysis such as known in the art.

Typically, in each application, an effective coating of the skin with primary active is achieved by topically applying (in terms of mg active/$cm^2$ skin) from about 0.0002 mg/$cm^2$ to about 0.4 mg/$cm^2$ of primary active to the skin to be treated. More preferably, from about 0.002 mg/$cm^2$ to about 0.2 mg/$cm^2$ of primary active is applied. Most preferably, from about 0.02 mg/$cm^2$ to about 0.1 mg/$cm^2$ of primary active is applied (the amount of composition that is applied may be, for example, from about 0.01 mg to about 5 mg composition/$cm^2$ skin, preferably about 1 to about 2 mg composition/$cm^2$ skin).

The compositions are generally applied by lightly massaging the composition into the skin, typically in the amounts described above.

The compositions of the invention can also be used for regulating oiliness of the scalp and for controlling dandruff. Methods of regulating scalp oiliness and for controlling dandruff are as described above, wherein the composition is applied to the scalp.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

Example 1

A water-in-oil topical composition suitable for use as a liquid make-up foundation is prepared from the following ingredients using conventional mixing and formulating techniques such as described below.

| Compounding code | Ingredient | Wt. % |
| --- | --- | --- |
| A | cyclomethicone | 9.25 |
| A | cetyl octanoate | 2.00 |
| A | dimethicone copolyol (DC3225C) | 20.00 |
| B | talc | 3.38 |
| B | pigment | 10.51 |
| B | Spheron L-1500 | 0.50 |
| C | Synthetic Wax Durachem 0602 | 0.10 |
| C | Arachidyl behenate | 0.30 |
| D | cyclomethicone | 1.00 |
| D | trihydroxystearin | 0.30 |
| E | laureth-7 | 0.50 |
| E | propyl paraben | 0.25 |
| F | fragrance | 0.05 |
| G | water | 34.44 |
| G | methyl paraben | 0.12 |
| G | propylene glycol | 8.00 |
| G | niacinamide | 4.00 |
| G | glycerin | 3.00 |
| G | sodium chloride | 2.00 |
| G | sodium dehydroacetate | 0.30 |

Combine the ingredients A and B in a suitable container. Mix the ingredients using a Silverson L4RT mixer equipped w/a 1" tubular assembly and a square hole screen for 30 minutes at 9000 rpm (the container can be covered to avoid loss of any volatile or other materials). Heat the resultant mixture to 85°–90° C. Add ingredients C, mix for 5 minutes at 2100 rpm using a Silverson L4RT mixer equipped w/a 2" head and a disintegrating screen. The container should be covered to minimize evaporation of cyclomethicone and other volatile or nonvolatile materials. Cool the resultant mixture to 45°–55° C.

Combine the ingredients D components and mix until a uniform slurry is formed. Separately, combine the ingredients E and mix until a uniform slurry is formed. Add the resultant slurries to the mixture of A, B and C (which is at 45°–55° C.), mix for 5 minutes at 2100 rpm using a Silverson L4RT equipped w/a 2" head and a disintegrating screen. Cool the resultant mixture to 30° C., then add ingredient F. Mix 5 minutes at 2100 rpm using a Silverson L4RT equipped w/a 2" head and a disintegrating screen.

Combine the ingredients G in a suitable container and mix until all components are dissolved. Slowly add the resultant solution to the mixture of A–F. Emulsify this combination using a Silverson L4RT mixer equipped w/a 2" head and a disintegrating screen at 2100–5100 rpm (rpms will increase as the mixture thickens), continue mixing for 5 minutes after all of the G mixture is added.

Apply the composition to a person's face once per day in an amount of 1–2 mg composition/$cm^2$ skin for four weeks, to observe a decrease in facial oil, a reduction in oily breakthrough, longer wear of the foundation, and more even coverage as the time period passes.

Other topical compositions suitable for use as a foundation are prepared in the above-described manner using pyridoxine, panthenol or pantothenic acid in place of niacinamide and are applied to the face as described above.

Example 2

A topical composition suitable for use as a liquid make-up foundation is prepared from the following ingredients using conventional mixing and formulating techniques.

| | wt % |
| --- | --- |
| dimethicone copolyol/cyclomethicone (Dow Corning QZ-3225C) | 10 |
| cyclomethicone (Dow Corning 344 fluid) | 17.74 |
| pigments | 3.7 |
| titanium dioxide | 8.25 |
| trihydroxy stearin | 0.3 |
| aqueous floral extract | 0.01 |
| denatured ethanol | 4–17 |
| salicylic acid | 1.45 |
| dipropylene glycol | 0–14 |
| PVP (polymeric dispersing agent) | 1 |
| procetyl AWS PPG-5 ceteteth, surfactant) | 3 |
| tri-sodium citrate | 0.3 |
| tetrasodium EDTA | 0.1 |
| glycerin | 10–30 |
| niacinamide | 4 |
| sodium chloride | 0.3 |
| water | 15.85–34.85 |

Apply the composition to a person's face once per day in an amount of 1–2 mg composition/$cm^2$ skin for four weeks, to observe a decrease in facial oil and/or shine, a reduction in oily breakthrough, longer wear of the composition, and more even coverage as time passes.

Other topical compositions suitable for use as a foundation are prepared in the above-described manner using pyridoxine, panthenol or pantothenic acid in place of niacinamide and are applied to the face as described above.

Example 3

Moisturizers having the compositions A, B or C are prepared from the following ingredients using conventional mixing and formulating techniques.

| Ingredient | A wt % | B wt % | C wt % |
| --- | --- | --- | --- |
| Water | 68.3 | 70.3 | 75.3 |
| niacinamide | 5 | 5 | 0 |
| Panthenol | 1.5 | 1.5 | 1.5 |
| acrylates copolymer (DC Polymer powder Q5-6603) | 2 | 0 | 0 |
| Octyl Methoxycinnamate (Parsol MCX) | 4 | 4 | 4 |
| Glycerin | 5 | 5 | 5 |
| Propylene Glycol | 1.1 | 1.1 | 1.1 |
| Isohexadecane (Permethyl 101 A) | 2 | 2 | 2.00 |
| Tocopheryl Acetate | 2 | 2 | 2.00 |
| herbal extract in propylene glycol & ethoxydiglycol | 1 | 1 | 1 |
| Butylene Glycol | 1 | 1 | 1 |
| Dimethicone (DC 200 Fluid 1000cs) | 1 | 1 | 1 |
| Cyclomethicone (DC 344 Silicone Fluid) | 1 | 1 | 1 |
| Triethanolamine | 0.8 | 0.8 | 0.8 |
| Cetyl Palmitate (Cutina CP) | 0.75 | 0.75 | 0.75 |
| Tribehenin (Syncrowax HRC) | 0.75 | 0.75 | 0.75 |
| Stearoxytrimethylsilane & Stearyl Alcohol (DC 580 Wax) | 0.5 | 0.5 | 0.5 |
| Phenoxyethanol | 0.62 | 0.62 | 0.62 |
| Carbomer (Carbopol 954) | 0.3 | 0.3 | 0.3 |
| Hectorite (Bentone EW) | 0.3 | 0.3 | 0.3 |
| Acrylates/C10–C30 Alkyl Acrylate Crosspolymer (Pemulen TR 1) | 0.2 | 0.2 | 0.2 |
| Potassium Cetyl Phosphate (Amphisol K) | 0.2 | 0.2 | 0.2 |
| Perfume | 0.2 | 0.2 | 0.2 |
| Disodium EDTA | 0.1 | 0.1 | 0.1 |
| Xanthan Gum | 0.07 | 0.07 | 0.07 |
| preservative | 0.25 | 0.25 | 0.25 |

Apply the composition to a person's face once per day in an amount of 1–2 mg composition/cm$^2$ skin for four weeks, to observe a decrease in facial oil and/or shine.

Other compositions are prepared in the above-described manner using pyridoxine, panthenol or pantothenic acid in place of niacinamide and are applied to the face as described above.

Example 4

A silicone gel containing 2 or 4% niacinamide is prepared from the following ingredients using conventional mixing and formulating techniques.

| | wt % |
| --- | --- |
| water | 89.6–91.6 |
| niacinamide | 2 or 4 |
| glycerin | 2.08 |
| cyclomethicone (Dow Corning 344 fluid) | 1.22 |
| butylene glycol | 1 |
| cyclomethicone and dimethiconol (Dow Corning Q2-1401) | 0.58 |
| cyclomethicone and dimethicone copolyol (Dow Corning QZ-3225C) | 0.58 |
| dimethicone copolyol (Dow Corning 193 polyether) | 0.12 |
| acrylates/C10–30 alkylacrylates crosspolymer (Pemulen TR-1) | 0.25 |
| carbomer (Carbopol 980) | 0.2 |
| DMDM hydantoin and iodopropynyl butyl carbamate (Glydant Plus) | 0.2 |
| disodium EDTA | 0.1 |

-continued

| | wt % |
| --- | --- |
| sodium hydroxide | 0.08–0.1 to total 100 |

Apply the gel to a person's face once per day in an amount of 1–2 m gel/cm$^2$ skin for four weeks, to observe a decrease in facial oil and/or shine.

Other silicone gels are prepared in the above-described manner using pyridoxine, panthenol or pantothenic acid in place of niacinamide and are applied to the face as described above.

Example 5

A liquid shampoo having the composition A, B or C is prepared by combining the following components using conventional mixing and formulating techniques:

| | A (wt %) | B (wt %) | C (wt %) |
| --- | --- | --- | --- |
| coconut oil | 14 | 18 | — |
| olive oil | 3 | — | — |
| castor oil | 3 | 4 | — |
| potassium hydroxide, 85% | 4.7 | 5.3 | — |
| glycerol | 2 | 4 | 5 |
| ethyl alcohol | 4 | — | 10 |
| sodium hexametaphosphate | 1 | — | — |
| perfume | 0.3 | 0.2 | q.s. |
| water | 64 | 64 | 36 |
| borax | — | 0.5 | — |
| coconut soap potassium salt | — | — | 35 |
| olive oil soft soap | — | — | 10 |
| niacinamide | 4 | 4 | 4 |

Apply the shampoo to the scalp every other day to once a day to reduce the appearance of oily hair and the occurrence of dandruff. A dose of about 0.5 ml is applied and washed off.

Other liquid shampoos are prepared in the above-described manner using pyridoxine, panthenol or pantothenic acid in place of niacinamide and are applied to the scalp as described above.

Example 6

A hair conditioner is prepared by combining the following components using conventional mixing and formulating techniques:

| | wt % |
| --- | --- |
| PVP K-30 (polymeric dispersing agent) | 3 |
| Neobee M-20 (propylene glycol dicaprylate) | 5 |
| Drewmulse 1128 (surfactant) | 5 |
| water | 69.5 |
| triethanolamine | |
| carbopol 934 (carbomer, polymeric thickening/dispersing agent) | 1 |
| WSP-X250 | 5 |
| Amerchol L-101 (mineral oil/lanolin oil) | 3 |
| Lipal 15 CSA | 3 |
| preservative | q.s. |
| perfume | 0.5 |
| niacinamide | 4 |

Apply the conditioner to the scalp, preferably to clean hair, every other day to once a day to reduce the appearance of oily hair and the occurrence of dandruff. Apply a dose of about 0.5 ml and wash off.

Other hair conditioners are prepared in the above-described manner using pyridoxine, panthenol or pantothenic acid in place of niacinamide and are applied as described above.

Example 7

A bath oil having the composition A, B or C is prepared by combining the following components using conventional mixing and formulating techniques:

|  | A (wt%) | B (wt%) | C (wt%) |
|---|---|---|---|
| POE 20 sorbitan monopalmitate | — | 5 | 22.2 |
| fragrance oil | 35 | 5 | 4.4 |
| isopropyl myristate | 65 | — | — |
| methyl p-hydroxybenzoate | — | 0.18 | — |
| propyl p-hydroxybenzoate | — | 0.02 | — |
| sodium lauryl sulfate | — | — | 10 |
| ninol AA-63 | — | — | 1 |
| sorbic acid | — | — | 0.2 |
| niacinamide | 4 | 4 | 4 |
| water q.s. | — | 100 | 100 |

Apply the bath oil to the skin either as prepared or in aqueous diluted form. Apply in a dose of from 1–2 mg oil /cm$^2$ skin for four weeks, to observe a decrease in skin oil and/or shine. Other bath oils are prepared in the above-described manner using pyridoxine, panthenol or pantothenic acid in place of niacinamide and are applied as described above.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method of regulating the oily and/or shiny appearance of mammalian skin, comprising the step of topically applying to the skin of a mammal needing such treatment a topical composition comprising:

(a) from about 1% to about 5% of an active for regulating the oily and/or shiny appearance of the skin, said active consisting essentially of one or more compounds selected from the group consisting of niacinamide, panthenol, and pantothenic acid; and (b) a cosmetically acceptable carrier for said active.

2. The method of claim 1 wherein from about 0.0002 mg to about 0.4 mg of said active per cm$^2$ of skin is topically applied.

3. The method of claim 2 wherein from about 0.002 mg to about 0.2 mg of said active per cm$^2$ of skin is topically applied.

4. The method of claim 3 wherein from about 0.02 mg to about 0.1 mg of said active per cm$^2$ of skin is topically applied.

5. The method of claim 1 wherein said active consists essentially of a mixture of (i) niacinamide and (ii) a compound selected from the group consisting of panthenol and pantothenic acid.

6. The method of claim 5 wherein said active consists essentially of a mixture of niacinamide and panthenol.

7. The method of claim 1 wherein said active consists essentially of niacinamide.

8. The method of claim 7 wherein said niacinamide is substantially pure niacinamide.

9. The method of claim 1 wherein said composition comprises from about 0.01% to about 20%, by weight, of said active.

10. The method of claim 9 wherein said composition comprises from about 2.5% to about 5%, by weight, of said active.

* * * * *